United States Patent
Watanabe et al.

(10) Patent No.: US 9,864,836 B2
(45) Date of Patent: Jan. 9, 2018

(54) COMPUTER PRODUCT, RENDERING APPARATUS, AND RENDERING METHOD

(71) Applicants: FUJITSU LIMITED, Kawasaki-shi, Kanagawa (JP); THE UNIVERSITY OF TOKYO, Tokyo (JP)

(72) Inventors: Masahiro Watanabe, Kawasaki (JP); Satoshi Fuchikami, Fukuoka (JP); Yoshimasa Kadooka, Kawasaki (JP); Toshiaki Hisada, Tokyo (JP); Seiryo Sugiura, Tokyo (JP); Takumi Washio, Tokyo (JP); Jun-ichi Okada, Tokyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 781 days.

(21) Appl. No.: 13/911,598

(22) Filed: Jun. 6, 2013

(65) Prior Publication Data
US 2013/0332126 A1    Dec. 12, 2013

(30) Foreign Application Priority Data
Jun. 8, 2012    (JP) .................................. 2012-131245

(51) Int. Cl.
*G06G 7/48*    (2006.01)
*G06F 19/00*    (2011.01)
(Continued)

(52) U.S. Cl.
CPC ........ *G06F 19/321* (2013.01); *G06F 17/5009* (2013.01); *G06T 19/00* (2013.01); *G06T 2219/008* (2013.01)

(58) Field of Classification Search
CPC .......... G06T 2207/30048; G06T 19/00; G06T 2207/10072; G06T 2207/10088;
(Continued)

(56) References Cited

U.S. PATENT DOCUMENTS 6,694,163 B1    2/2004  Vining
2003/0099386 A1    5/2003  Schneider et al.
(Continued)

OTHER PUBLICATIONS

Smolka_2005 (Watershed based region growing algorithm, Annales UMCS Informatica AI 3 (2005) 169-178).*
(Continued)

*Primary Examiner* — Kamini S Shah
*Assistant Examiner* — Brian S Cook
(74) *Attorney, Agent, or Firm* — Staas & Halsey LLP (57) ABSTRACT

A computer-readable recording medium stores a rendering program that renders simulation results and causes a computer to execute a process that includes detecting a range of physical values of a rendering element group to be rendern and of an area specified in a simulation model that is a set of elements each having a physical value for each position to be simulated; identifying from the simulation model, an adjacent element group that is a set of elements adjacent to rendering elements included in the rendering element group; determining whether the physical value of each adjacent element included in the adjacent element group is within the range; adding to the rendering element group, an adjacent element for which the physical value is determined to be included in the range; and rendering the simulation model according to the rendering element group to which the adjacent element has been added.

5 Claims, 7 Drawing Sheets

(51) Int. Cl.
*G06T 19/00* (2011.01)
*G06F 17/50* (2006.01)

(58) Field of Classification Search
CPC . G06T 2207/20141; G06T 2207/20148; G06T 2210/41; G06T 7/0012; G06T 7/0014; G06T 7/0081; G06T 7/0095; G06T 7/0097; G06T 7/602; G06T 2219/008; G06F 19/321; G06F 17/5009
USPC .......................................................... 703/6
See application file for complete search history.

(56) References Cited

U.S. PATENT DOCUMENTS

| | | | | |
|---|---|---|---|---|
| 2004/0130546 | A1* | 7/2004 | Porikli | G06K 9/342 345/423 |
| 2010/0232668 | A1* | 9/2010 | Schobinger | G06T 7/13 382/131 |
| 2012/0121151 | A1* | 5/2012 | Bernhardt | A61B 6/03 382/131 |

OTHER PUBLICATIONS

Lehmann_2005 (Segmentation of medical images combining local, regional, global, and hierarchical distance into a bottom-up region merging scheme, Proc. SPIE Symposium on Medical Imaging (MI'05): Image Processing, vol. 5747 (56)).*
Processing_Binary_Images (The Image Processing Handbook, Fourth Edition, Processing Binary Images, Chapter 7: CRC Press LLC 2002).*
Otsu_1979.pdf Otsu, N., A Threshold Selection Method from Gray-Level Histograms, IEEE 1997.*
Standard_Deviation_2012.pdf Standard Deviation Defined, Archived Wikipedia dated Jun. 7, 2012 downloaded from https://en.wikipedia.org/w/index.php?title=Standard_deviation&oldid=496448883.*
Reed_2007.pdf Reed, J., Mean and Standard Deviation dated 2007 downloaded from http://staff.argyll.epsb.ca/jreed/math30p/statistics/standardDeviation.htm.*
Tetrahedron_In_Cube_2011.pdf, Tetrahedron in Cube archived in the waybackmachine dated Nov. 14, 2011 Downloaded from http://www.cut-the-knot.org/Curriculum/Geometry/Polyhedra/tetrahedronInCube.shtml.*
Leng_2011.pdf Leng, J., A Novel Geometric Flow-Driven Approach for Quality Improvement of Segmented Tetrahedral Meshes, International Meshing Roundtable, 2011.*
Oakes_2009.pdf Oakes, R.S., et al Detection and Quantification of Left Atrial Structural Remodeling With Delayed-Enhancement Magnetic Resonance Imaging in Patients with Atrial Fibrillation, American Heart Association, 2009 DOI: 10.1161/CIRCULATIONAHA.108.811877.*
Sekiguchi_1994.pdf Sekiguchi, H., Interactive 3-Dimensional Segmentation Method Based on Region Growing Method, Systems and Computers in Japan, vol. 25, No. 1, 1994.*
Revol_1997 (A New Minimum Variance Region Growing Algorithm for Image Segmentation, Pattern Recognition Letters 18 (1997) 249-258).*
Render defined Webster's II New Riverside University Dictionary, 1994.*
Mesh_Generation_1997 (ICE Theory Group: ICE 280G, Spring 1997: Mesh Generation for Graphics and Scientific Computation).*
"vtkMarchingContourFilter Class Reference.pdf," KITWARE, inc., Sep. 27, 2010 searched on Mar. 12, 2012 at [URL] www.vtk.org/doc/release/5.6/html/a01103.html.
Sivewright et al., "Interactive region and volume growing for segmenting volumes in MR and CT images", Med. Inform., vol. 19, No. 1, Taylor and Francis Ltd., Basingstoke, GB, 1994, pp. 71-80.
Day et al., "A region growing method for tumor volume segmentation on PET images for rectal and anal cancer patients", Medical Physics, vol. 36, No. 10, AIP, Melville, NY, US, Sep. 4, 2009, pp. 4349-4358.
Extended European Search Report issued by the European Patent Office dated Nov. 3, 2017 in corresponding European patent application No. 13170630.1.

* cited by examiner

| ID | FIRST VERTEX | SECOND VERTEX | THIRD VERTEX | FOURTH VERTEX | CENTER OF GRAVITY | PHYSICAL VALUE |
|---|---|---|---|---|---|---|
| t1 | v1(t1) | v2(t1) | v3(t1) | v4(t1) | g(t1) | e(t1) |
| t2 | v1(t2) | v2(t2) | v3(t2) | v4(t2) | g(t2) | e(t2) |
| : | : | : | : | : | : | : |
| ti | v1(ti) | v2(ti) | v3(ti) | v4(ti) | g(ti) | e(ti) |
| : | : | : | : | : | : | : |
| tN | v1(tN) | v2(tN) | v3(tN) | v4(tN) | g(tN) | e(tN) |

| ID | FIRST VERTEX | SECOND VERTEX | THIRD VERTEX | FOURTH VERTEX | CENTER OF GRAVITY | PHYSICAL VALUE | SELEC-TION |
|---|---|---|---|---|---|---|---|
| r1 | v1(r1) | v2(r1) | v3(r1) | v4(r1) | g(r1) | e(r1) | 0 |
| r2 | v1(r2) | v2(r2) | v3(r2) | v4(r2) | g(r2) | e(r2) | 0 |
| : | : | : | : | : | : | : | : |
| rj | v1(rj) | v2(rj) | v3(rj) | v4(rj) | g(rj) | e(rj) | 0 |
| : | : | : | : | : | : | : | : |
| rM | v1(rM) | v2(rM) | v3(rM) | v4(rM) | g(rM) | e(rM) | 0 |

| ID | FIRST VERTEX | SECOND VERTEX | THIRD VERTEX | FOURTH VERTEX | CENTER OF GRAVITY | PHYSICAL VALUE |
|---|---|---|---|---|---|---|
| w1 | v1(w1) | v2(w1) | v3(w1) | v4(w1) | g(w1) | e(w1) |
| w2 | v1(w2) | v2(w2) | v3(w2) | v4(w2) | g(w2) | e(w2) |
| : | : | : | : | : | : | : |
| wk | v1(wk) | v2(wk) | v3(wk) | v4(wk) | g(wk) | e(wk) |
| : | : | : | : | : | : | : |
| wK | v1(wK) | v2(wK) | v3(wK) | v4(wK) | g(wK) | e(wK) |

COMPUTER PRODUCT, RENDERING APPARATUS, AND RENDERING METHOD

CROSS REFERENCE TO RELATED APPLICATIONS

This application is based upon and claims the benefit of priority of the prior Japanese Patent Application No. 2012-131245, filed on Jun. 8, 2012, the entire contents of which are incorporated herein by reference.

FIELD

The embodiment discussed herein is related to a computer product, a rendering apparatus, and a rendering method.

BACKGROUND

The heart in humans and animals is an internal organs that pumps blood and this function of the heart is conventionally reproduced by numerical analysis. In the numerical analysis of the heart, myocardial infarction, which causes changes over time at an arbitrary area of the heart, is simulated. When changes of such an area are to be viewed, a technique of extracting data corresponding to the area of the heart can be used (see, for example, Kitware, Inc., vtkMarchingContourFilter Class Reference.pdf, Sep. 27, 2010, retrieved Mar. 12, 2012: [URL]www.vtk.org/doc/release/5.6/html/a01103.html).

Nonetheless, with the technique above, an allowable range of an upper limit and a lower limit of physical values, which are elements of an arbitrary area and are for workrate and pressure, are specified as a myocardial infarcted area by a user. The allowable range of the physical values identifying the myocardial infarcted area varies according to patient and consequently, specification of an allowable range for a myocardial infarction is difficult. Such a problem is not limited to the heart and is similar for other internal organs as well as other disorders other than myocardial infarctions.

SUMMARY

According to an aspect of an embodiment, a computer-readable recording medium stores a rendering program that renders simulation results and causes a computer to execute a process that includes detecting a range of physical values of a rendering element group to be rendered and of an area specified in a simulation model that is a set of elements each having a physical value for each position to be simulated; identifying from the simulation model, an adjacent element group that is a set of elements adjacent to rendering elements included in the rendering element group; determining whether the physical value of each adjacent element included in the adjacent element group is within the range; adding to the rendering element group, an adjacent element for which the physical value is determined to be included in the range; and rendering the simulation model according to the rendering element group to which the adjacent element has been added.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Preferred embodiments of a rendering program, a rendering apparatus, and a rendering method according to the present invention will be explained in detail with reference to the accompanying drawings. In the present embodiments, although description is given using a 3-dimensional model of a heart as one example of an internal organ, implementation may be by a 3-dimensional model of another internal organ other than the heart.

FIGS. 1A, 1B, 1C, and 1D are diagrams depicting a rendering example of a heart model by a rendering apparatus according to an embodiment. Among FIGS. 1A, 1B, 1C, and 1D, FIG. A depicts a 3-dimensional model of a heart (hereinafter, "heart model"). A heart model 100, for example, is a set of tetrahedral elements (unstructured grid data) called tetra elements. Each tetra element has a physical value corresponding to the position of the tetra element. A physical value is a value indicative of the behavior of the cardiac muscle corresponding to the tetra element; and, for example, pressure [KPa], work [J/ml], workrate [J/s·ml] are adopted as physical values.

Figure 1A:
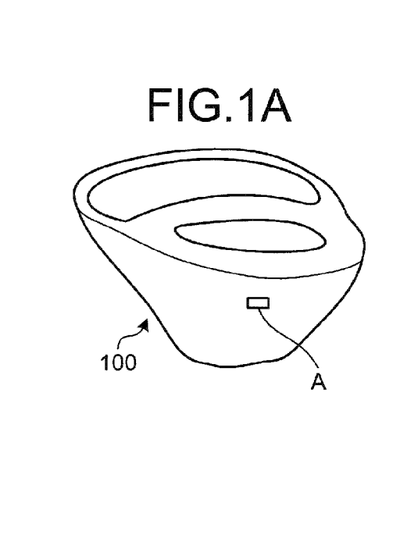
FIGS. 1A, 1B, 1C, and 1D are diagrams depicting a rendering example of a heart model by a rendering apparatus according to an embodiment.

The rendering apparatus, consequent to manipulation of a pointing device by a user, specifies an area in the heart model 100. The specified area is referred to as a "specified area". For example, the rendering apparatus maps onto an external surface of the heart model 100, the rectangular area specified by the user and thereby, sets an external surface of heart model, corresponding to the rectangular area, to be a specified area A.

Figure 1B:
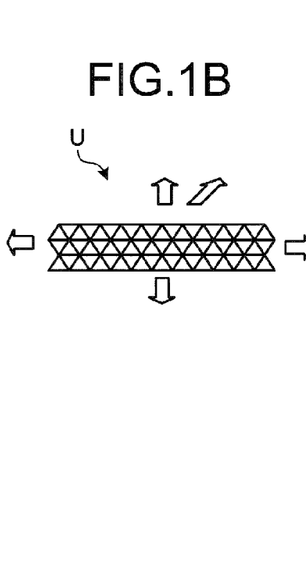

FIG. 1B is an enlarged view of the specified area A specified in FIG. 1A. The specified area A includes a tetra element group. The tetra element group within the specified area A is called a rendering element group U. In FIG. 1B, triangular shapes represent tetra elements. Although the tetra elements are tetrahedrons, herein, for the sake of convenience, each is regarded as a triangle. The rendering apparatus expands the specified area A in the proximal directions of the tetra elements, indicated by the arrows.

In this example, adjacent elements having physical values within an allowable range between upper and lower limits of the physical values of the initial rendering element group U in FIG. 1B, are included in the rendering element group U.

Figure 1C:
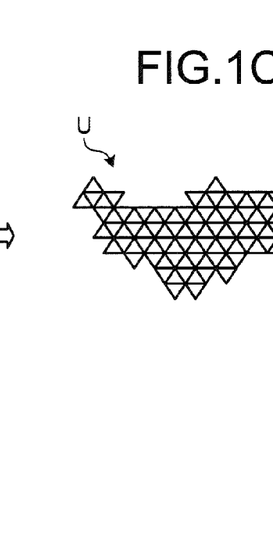

Further, even adjacent elements outside the allowable range are included in the rendering element group U, under a given condition described hereinafter. FIG. 1C depicts the rendering element group U after expansion. The rendering element group U post-expansion is the area displaying a disorder, such as a myocardial infarction, that is to be viewed.

Figure 1D:
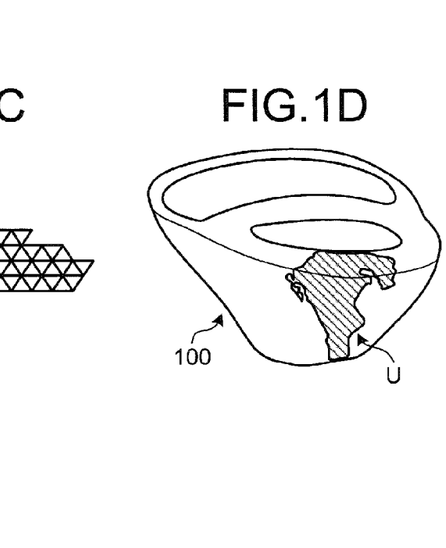

FIG. 1D is a rendering example of the heart model 100, characterizing the rendering element group U post-expansion depicted in FIG. 1C. In this manner, by merely specifying the specified area A as depicted in FIG. 1A, an area afflicted by a disorder, such as a myocardial infarction, that varies according to patient as well as according to the state of a patient can be easily identified.

Figure 2:
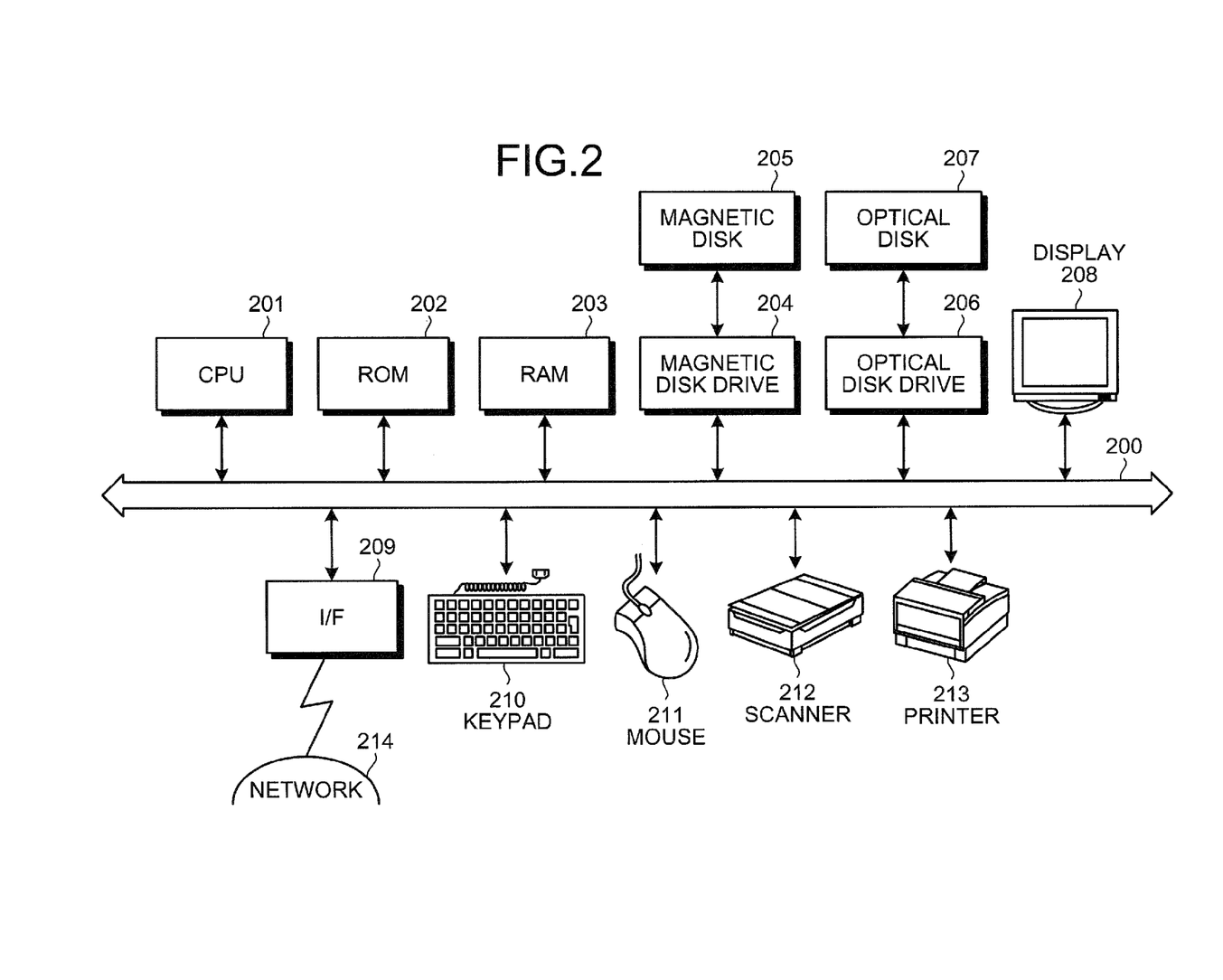
FIG. 2 is a block diagram of a hardware configuration of the rendering apparatus according to the embodiment.

FIG. 2 is a block diagram of a hardware configuration of the rendering apparatus according to the embodiment. As depicted in FIG. 2, the rendering apparatus includes a central processing unit (CPU) 201, read-only memory (ROM) 202, random access memory (RAM) 203, a magnetic disk drive 204, a magnetic disk 205, an optical disk drive 206, an optical disk 207, a display 208, an interface (I/F) 209, a keypad 210, a mouse 211, a scanner 212, and a printer 213, respectively connected by a bus 200.

The CPU 201 governs overall control of the rendering apparatus. The ROM 202 stores various types of programs such as a boot program. The RAM 203 is used as a work area of the CPU 201. The magnetic disk drive 204, under the control of the CPU 201, controls the reading and writing of data with respect to the magnetic disk 205. The magnetic disk 205 stores data written thereto under the control of the magnetic disk drive 204.

The optical disk drive 206, under the control of the CPU 201, controls the reading and writing of data with respect to the optical disk 207. The optical disk 207 stores data written thereto through the optical disk drive 206, the data being read out through the optical disk drive 206 by a computer.

The display 208 displays, for example, data such as text, images, functional information, etc., in addition to a cursor, icons, and/or tool boxes. A liquid crystal display, a plasma display, etc., may be employed as the display 508.

The I/F 209 is connected to a network 214 such as a local area network (LAN), a wide area network (WAN), and the Internet through a communication line and is connected to other apparatuses through the network 214. The I/F 209 administers an internal interface with the network 214 and controls the input/output of data from/to external apparatuses. For example, a modem or a LAN adaptor may be employed as the I/F 209.

The keypad 210 includes, for example, keys for inputting letters, numerals, and various instructions and performs the input of data. Alternatively, a touch-panel-type input pad or numeric keypad, etc. may be adopted. The mouse 211 is used to move the cursor, select an allowable range, or move and change the size of windows. A track ball or a joy stick may be adopted provided each respectively has a function similar to a pointing device.

The scanner 212 optically reads an image into the rendering apparatus. The scanner 212 may have an optical character reader (OCR) function. The printer 213 prints image data and text data. The printer 213 may be, for example, a laser printer, an inkjet printer, and the like. Further, configuration may be such that at least any one among the optical disk drive 206, the optical disk 207, the display 208, the keypad 210, the mouse 211, the scanner 212, and the printer 213 is omitted.

Figure 3:
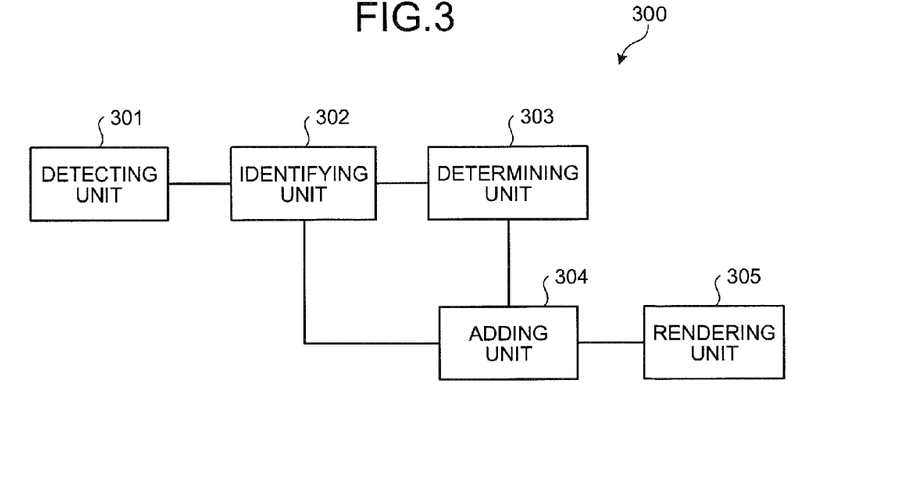
FIG. 3 is a block diagram of a functional configuration of the rendering apparatus according to the embodiment.

FIG. 3 is a block diagram of a functional configuration of the rendering apparatus according to the embodiment. A rendering apparatus 300 includes a detecting unit 301, an identifying unit 302, a determining unit 303, an adding unit 304, and a rendering unit 305. Functions of the detecting unit 301, the identifying unit 302, the determining unit 303, the adding unit 304, and the rendering unit 305 are, for example, implemented by executing on the CPU 201, a program stored in a storage device such as the ROM 202, the RAM 203, the magnetic disk 205, and the optical disk 207 depicted in FIG. 2, or by the I/F 209.

The detecting unit 301 detects for each position to be simulated and detects in a simulation model that is a set of elements respectively having a physical value, physical values of the rendering element group U, which is the specified area to be rendered. For example, the detecting unit 301 detects an allowable range of physical values of the rendering element group U within the specified area A in an internal organ model, which is a set of elements having physical values according to each position in the internal organ. The data structure of the rendering element group U within the specified area A in the internal organ model, for example, is a portion of the data structure of the tetra element group making up the heart model 100.

Figure 4:
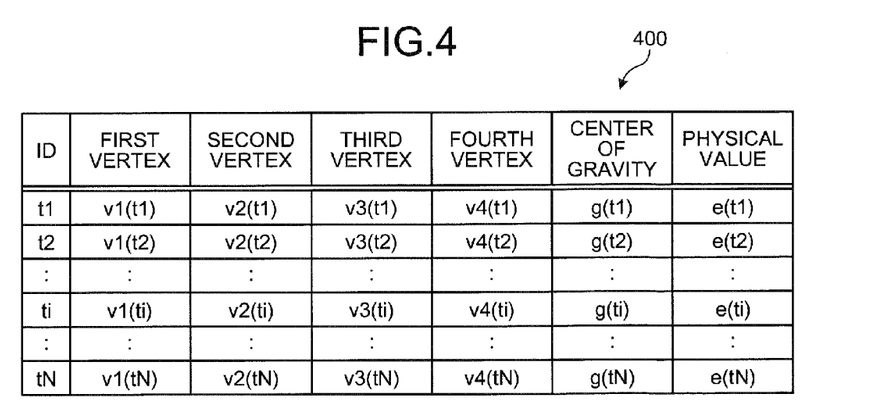
FIG. 4 is a diagram depicting a data structure example of a rendering element group.

FIG. 4 is a diagram depicting a data structure example of the rendering element group U. A data structure 400 of the rendering element group U is a data structure having values respectively for an ID field, a first vertex field to a fourth vertex field, a center of gravity field, and a physical value field.

The ID field stores an ID of a tetra element within the specified area A, where ID: i ($1 \leq i \leq n$). An ID is identifier information uniquely identifying a tetra element. A tetra element of the ID "i" is a tetra element ti. The first vertex field to the fourth vertex field store vertex coordinate values for the first vertex v1(ti) to the fourth vertex v4(ti) of the tetra element ti. For the sake of convenience, coordinate values are indicated as v1(ti) to v4(ti). The first vertex v1(ti) to the fourth vertex v4(ti) are respective vertices of a tetra element, which is a tetrahedron.

The center of gravity field stores center of gravity coordinate values for the center of gravity g(ti) of the tetra element ti. For the sake of convenience, the coordinate values will be indicated as g(ti). The physical value field stores a physical value e(ti) assigned to the tetra element ti. As described, a physical value is a value indicative of the behavior of the cardiac muscle corresponding to the tetra element; and, for example, pressure [KPa], work [J/ml], workrate [J/s·ml] are adopted as physical values.

Figure 5:
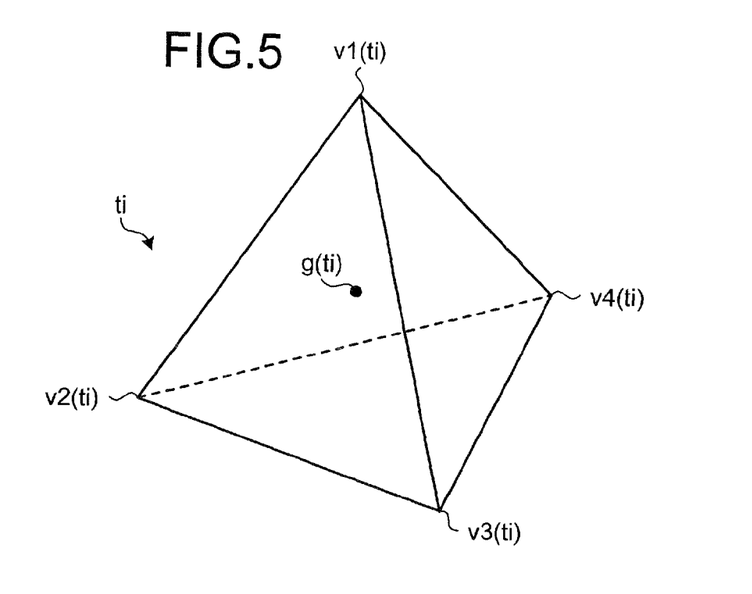
FIG. 5 is a diagram depicting a tetra element ti depicted in FIG. 4.

FIG. 5 is a diagram depicting the tetra element ti depicted in FIG. 4. The shape of the tetra element ti is a tetrahedron having the first vertex v1(ti) to the fourth vertex v4(ti). Further, at the center of gravity g(ti), a physical value e(ti) is assigned.

Reference of the description returns to FIG. 3. The detecting unit 301 extracts the physical values of the tetra elements of the rendering element group U within the specified area A as depicted in FIG. 1A. For example, the detecting unit 301 generates a histogram of the physical values that the tetra elements of the rendering element group U have and detects the upper and lower limit physical values.

Figure 6:
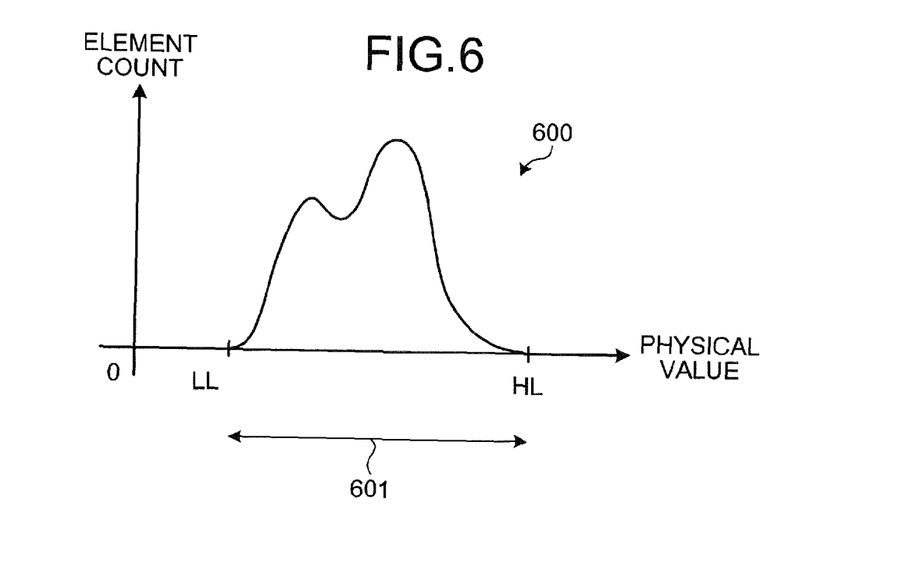
FIG. 6 is a diagram depicting an example of a histogram.

FIG. 6 is a diagram depicting an example of a histogram. The detecting unit 301, for example, detects in a histogram 600, an allowable range 601 from an upper limit HL to a lower limit LL. Herein, the upper limit HL is the largest physical value and the lower limit LL is the smallest physical value. Further, the upper limit HL may be the largest physical value when the element count is greater than or equal to a given count. Similarly, the lower limit LL may be the smallest physical value when the element count is greater than or equal to the given count. Further, the allowable range 601 may be expanded by a preliminarily set allowance value. For example, when the allowable range 601 is [LL, HL] and an allowance value α(>0) is assumed, the allowable range 601 becomes [LL-α, HL+α].

Reference of the description returns to FIG. 3. The identifying unit 302 identifies from the simulation model, an adjacent element group, which is a set of elements adjacent to the elements that are to be rendered and that are included in the rendering element group U. For example, the identifying unit 302 identifies from an internal organ model, an adjacent element group, which is a set of elements adjacent to the elements of the rendering element group U. For example, the identifying unit 302 identifies an adjacent element group from the heart model 100. An adjacent element is a tetra element that is adjacent to a given tetra element, such as a tetra element that is in contact with a face, edge, and/or vertex of the given tetra element. The identified adjacent element group is stored in the data structure depicted in FIG. 7, to a storage device.

Figure 7:
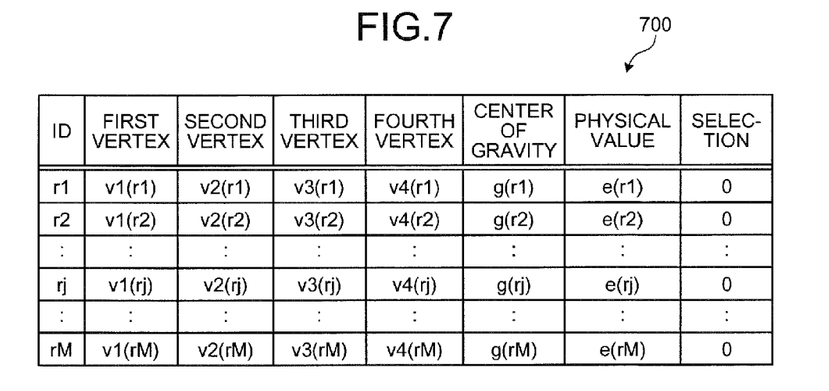
FIG. 7 is a diagram depicting a data structure example of an adjacent element group.

FIG. 7 is a diagram depicting a data structure example of an adjacent element group. A data structure 700 of an adjacent element group is a data structure that in addition to the fields configuring the data structure 400 of the rendering element group U, further includes a selection field. Description of the fields identical to those configuring the data structure 400 of the rendering element group U will be omitted herein.

The selection field stores a selection flag indicating whether the adjacent element has been selected. Here, as an example, a value of "1" indicates that the adjacent element has been selected, and a value of "0" indicates that the adjacent element has not been selected. In FIG. 7, an initial state is depicted where all values are "0" indicating that no adjacent element has been selected yet.

Reference of the description returns to FIG. 3. The determining unit 303 determines whether the physical values of the adjacent elements included in the identified adjacent element group are with the range described above. For example, the determining unit 303 determines whether the physical values of the elements of the adjacent element group identified by the identifying unit 302 are within the allowable range 601. For example, the determining unit 303 selects from the adjacent element group data structure 700 depicted in FIG. 7, adjacent elements 1 record at a time. The selection flag of the selected adjacent element changes from "0" to "1". The determining unit 303 determines whether the physical element of the selected adjacent element is within the allowable range 601 detected by the detecting unit 301.

The adding unit 304 adds to the rendering element group U, adjacent elements for which the physical value thereof has been determined to be within the range. For example, the adding unit 304 adds to the rendering element group U, elements determined by the determining unit 303 to be within the allowable range 601. For example, the adding unit 304 adds to the data structure of an additional element group, adjacent elements for which the physical value thereof has been determined to be within the allowable range 601.

Figure 8:
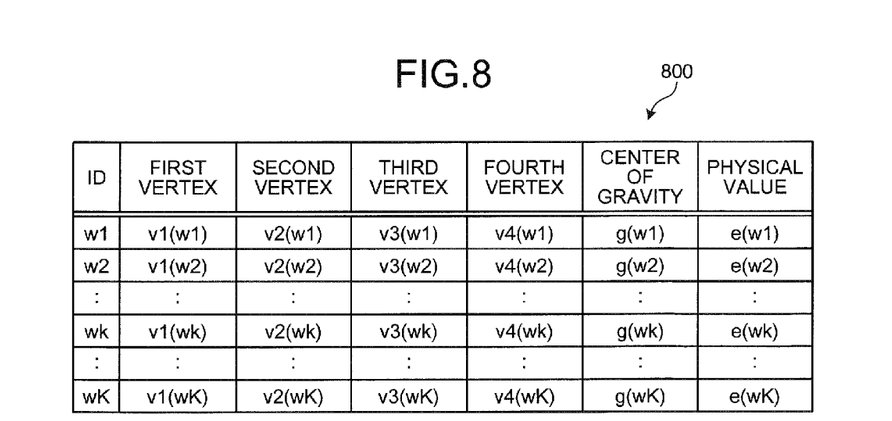
FIG. 8 is a diagram depicting a data structure example of an additional element group.

FIG. 8 is a diagram depicting a data structure example of an additional element group. A data structure 800 of an additional element group has fields identical to those configuring the data structure 400 of the rendering element group U and therefore, description will be omitted. An additional element wk is a tetra element that is among an adjacent element group and whose physical value is within the allowable range 601.

Reference of the description returns to FIG. 3. When among an adjacent element group, an element of an element group determined to be outside the allowable range 601 contacts multiple elements in the rendering element group U and the adjacent element group, the adding unit 304 adds the element to the rendering element group U. For example, if an adjacent element (whose physical value is outside the allowable range 601) is surrounded by multiple tetra elements in the rendering element group U post-addition, the adding unit 304 considers the physical value thereof to be within the allowable range 601, and as an additional element, adds the adjacent element to the data structure 800 of the additional element group.

In a simulation generating the heart model 100, by segmentizing the tetra elements, tetra elements whose physical value is outside the allowable range 601 are discretely among the group of the tetra elements whose physical values are within the allowable range 601. Meanwhile, since the afflicted site, such as that of a myocardial infarction, to be viewed by the user has continuity, to guarantee the continuity of the rendering element group U, even if the physical value of an adjacent element is outside the allowable range 601, but the adjacent element contacts multiple tetra elements of the rendering element group U (including added elements), the adjacent element is regarded as an additional element.

Here, contact with the multiple tetra elements includes, for example, contact between faces, contact between edges, and contact between vertices. Definitions of the types of contact with the multiple tetra elements are determined by a setting. Among contact between faces, edges, and vertices, contact sites between faces are the most abundant whereas contact sites between vertices are the fewest. Therefore, concerning contact with the multiple tetra elements, contact with each of the elements only at faces may be considered to be contact with the multiple elements. Further, contact with each of the tetra elements at faces or edges may be considered to be contact with the multiple elements. Contact by any among faces, edges, and vertices may be considered contact with the multiple tetra elements.

The adding unit 304, if an element of the element group determined to be outside the allowable range 601 is within a given distance from at least any one among the multiple elements, adds the element to the rendering element group U. For example, if the distance between the center of gravity of a given tetra element of the element group determined to be outside the allowable range 601 and the center of gravity of at least any one tetra element among contacting elements to be rendered is within a given distance, the adding unit 304 adds to the rendering element group U, the given tetra element of the element group that has been determined to be outside the allowable range 601. In other words, if the given tetra element is a given distance away or more from the multiple tetra elements, the adding unit 304 does not regard the given tetra element as an additional element. Thus, by prescribing a restriction based on a given distance, excessive expansion of the rendering element group U can be controlled and the accuracy of automatically identifying the specified area A can be improved.

In this example, a restriction is assumed where a given element of the element group that has been determined to be outside the allowable range 601 is within a given distance from at least any one element among the multiple elements and therefore, the restriction may be that the given element is with an given distance of each of the multiple elements.

The rendering unit 305 renders a simulation model according to the rendering element group U to which adjacent elements have been added. For example, the rendering unit 305 renders an internal organ model, based on the rendering element group U after the addition by the adding unit 304. For example, the rendering unit 305 renders the rendering element group U. Thus, the user can confirm the 3-dimensional shape of an afflicted site. Further, configuration may be such that the rendering unit 305 renders the heart model 100 and renders the rendering element group U of the heart model 100 depicted with more emphasis. As a result, the user can confirm the extent of the afflicted area in the heart model 100. Further, configuration may be such that the rendering unit 305 renders a remaining element group that is exclusive of the rendering element group U of the heart model 100, whereby the user can confirm the heart model 100 that excludes the afflicted site and/or a border of the afflicted site.

Further, configuration may be such that if the additional element group has become exhausted, the rendering unit 305 renders the internal organ model based in the rendering element group U post-addition. As a result, automatic expansion of the specified area A is suspended. On the other hand, if the additional element group is present, the rendering unit 305 does not yet render the internal organ model. In this case, the identifying unit 302 identifies an adjacent element group that is adjacent to the elements in a tetra element group that is to be added. For example, the identifying unit 302 adds the newly identified adjacent element group to the data structure of the adjacent element group. In this case, the selection flag is set to "0" and therefore, the determining unit 303 and the adding unit 304 perform a determination process and an addition process with respect to the newly identified adjacent element group. Thus, the specified area A can be automatically expanded.

Figure 9:
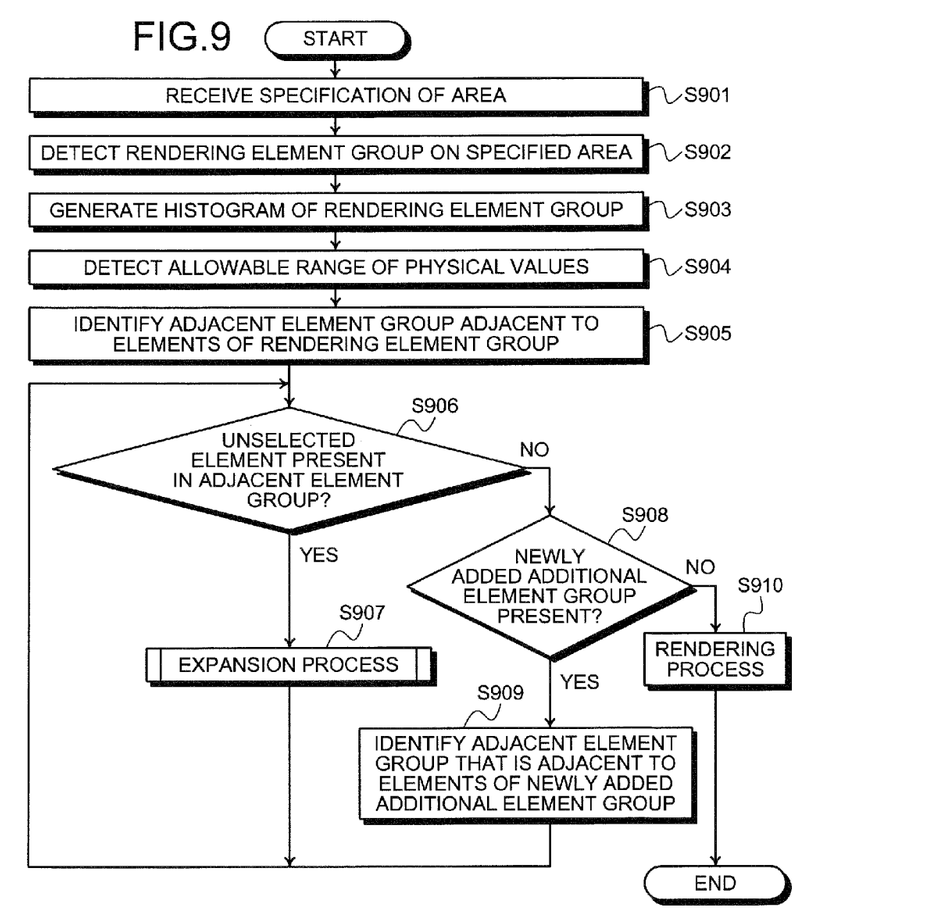
FIG. 9 is a flowchart depicting an example of a rendering process performed by the rendering apparatus according to the embodiment.

FIG. 9 is a flowchart depicting an example of a rendering process performed by the rendering apparatus 300 according to the embodiment. The rendering apparatus 300 receives via user operation, specification of an area of the heart model 100 (step S901), and detects the rendering element group U on the specified area A (step S902). The rendering apparatus 300 generates the histogram 600 of the physical values of the rendering element group U (step S903), and detects the allowable range 601 of the physical values (step S904).

The rendering apparatus 300 identifies an adjacent element group adjacent to elements of the rendering element group U (step S905), and determines whether an unselected element is present in the adjacent element group (step S906). If an unselected element is present (step S906: YES), the rendering apparatus 300 executes an expansion process (step S907), and returns to step S906. Details of the expansion process (step S907) will be described hereinafter with reference to FIG. 10. Thus, for each unselected element, the expansion process (step S907) is executed.

At step S906, if no unselected element is present (step S906: NO), the rendering apparatus 300 determines whether a newly added additional element group is present (step S908). If a newly added additional element group is present (step S908: YES), the rendering apparatus 300 identifies an adjacent element group that is adjacent to the elements of the newly added additional element group (step S909), and returns to step S906. Thus, the rendering apparatus 300 identifies adjacent element groups until no newly added additional element group is obtained and thus, can expand the rendering element group U.

At step S908, if no newly added additional element group is present (step S908: NO), the rendering apparatus 300 executes a rendering process via the rendering unit 305 (step S910). As a result, display of an afflicted area of the heart model 100 can be displayed as depicted in FIG. 1D.

Figure 10:
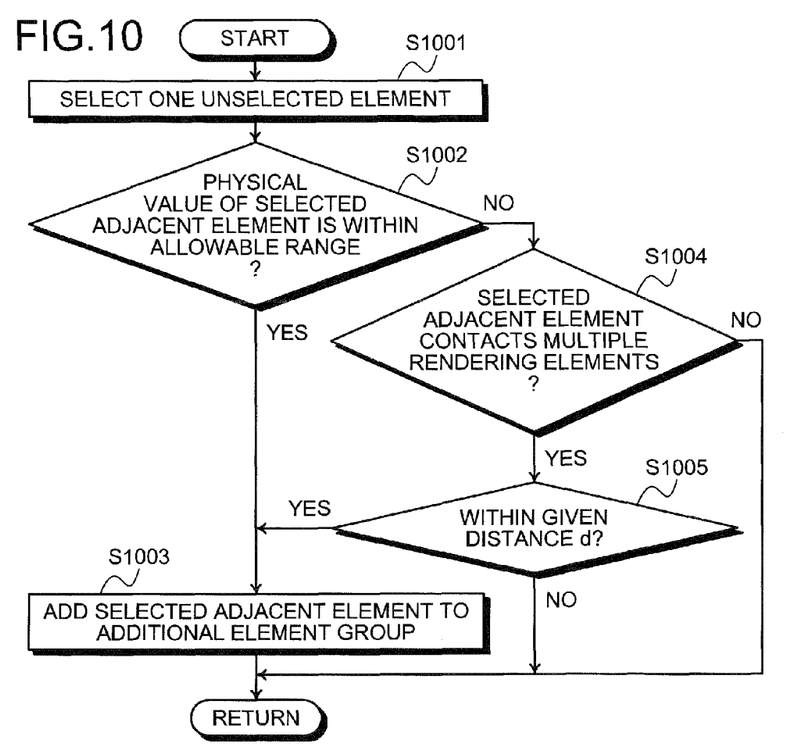
FIG. 10 is a flowchart of an example of an expansion process (step S907) depicted in FIG. 9.

FIG. 10 is a flowchart of an example of the expansion process (step S907) depicted in FIG. 9. The rendering apparatus 300 selects one unselected element from among the adjacent element group (step S1001). In other words, the rendering apparatus 300 selects a tetra element whose selection flag is "0". Herein, the selected adjacent element is referred to as a "selected adjacent element". Through this selection, the selection flag changes from "0" to "1". The rendering apparatus 300 determines whether the physical value of the selected adjacent element is within the allowable range 601 (step S1002). If the physical value is within the allowable range 601 (step S1002: YES), the rendering apparatus 300 adds the selected adjacent element to the data structure of the additional element group (step S1003), and proceeds to step S906. As a result, the selected adjacent element is added to the rendering element group U, enabling the rendering element group U to be expanded.

On the other hand, at step S1002, if the physical value of the selected adjacent element is outside the allowable range 601 (step S1002: NO), the rendering apparatus 300 determines whether the selected adjacent element contacts multiple rendering elements (step S1004). If the selected adjacent element contacts multiple rendering elements (step S1004: YES), the rendering apparatus 300 determines whether the distance between the selected adjacent element and any one of the multiple tetra elements of the specified area A with which contact is made, is within a given distance d (step S1005).

If the distance is within the given distance d (step S1005: YES), the rendering apparatus 300 proceeds to step S1003, and adds the selected adjacent element to the data structure of the additional element group (step S1003). Thus, even if the physical value is outside the allowable range 601, the continuity of the afflicted site can be guaranteed.

At step S1005, if the distance is not within the given distance d (step S1005: NO), the rendering apparatus 300 proceeds to step S906, without adding the selected adjacent element to the data structure of the additional element group. Consequent to the condition of the distance having to be within the given distance d, excessive expansion of the rendering element group U can be suppressed.

Further, at step S1004, if the selected adjacent element does not contact multiple rendering elements (step S1004: NO), the rendering apparatus 300 proceeds to step S906, without adding the selected adjacent element to the data structure of the additional element group, and ends the expansion process (step S907).

In this manner, according to the embodiment, an afflicted site can be easily identified. For example, by merely specifying, as the specified area A, a location to be viewed, the user can automatically expand the rendering elements suitable for the afflicted site without a need for identifying the afflicted area for each patient or each state of one patient.

Further, even if the physical value of the selected adjacent element is outside the allowable range 601, the selected adjacent element can be considered to be a tetra element whose physical value is within the allowable range 601 based on a given condition, thereby enabling the continuity of the afflicted site to be guaranteed. In this case, if the distance to a rendering element is not within a given distance, the tetra element is not considered to be within the allowable range 601 and thus, the rendering apparatus 300 can suppress excessive expansion of the rendering element group U. Consequently, the rendering apparatus 300 can facilitate improved identification accuracy of the specified area A.

Further, when the tetra elements to be added to the rendering elements have been exhausted, the expansion process ends. Thus, by merely specifying the specified area A initially and without having to determine the size of the afflicted site, the user can obtain, as the afflicted site, the rendering element group U that is ultimately expanded, enabling identification of the afflicted site to become more convenient.

The present invention facilitates identification of an afflicted site in an internal organ.

All examples and conditional language provided herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable recording medium storing a rendering program upon being performed by a processor provided in a computer to cause the processor to render calculation results of a heart model on a display device coupled to the computer and causes the processor to execute a process comprising:

generating a histogram of physical values of tetra elements of a rendering element group to be rendered and specified in the heart model including a set of tetra elements each having a physical value for each position to be simulated to detect an allowable range of the physical values, the physical values being values indicative of a behavior of a cardiac muscle of the heart model corresponding to the tetra elements;

identifying from the heart model, an adjacent element group that is a set of tetra elements adjacent to rendering elements included in the rendering element group;

determining whether the physical value of each adjacent element included in the identified adjacent element group is within the allowable range;

adding to the rendering element group, an adjacent tetra element for which the physical value has been determined to be included in the allowable range, the adding including adding to the rendering element group, a tetra element only when the tetra element contacts multiple tetra elements in the rendering element group, the tetra element being of an element group that is among the adjacent element group and determined to be outside the allowable range and the center of gravity of at least any one tetra element among the multiple tetra elements determined to be rendered within a designated distance; and rendering the heart model on the display device according to the rendering element group to which the adjacent element has been added, wherein the rendering the heart model includes rendering the heart model based on the rendering element group post-addition when an element group added to the rendering element group is exhausted.

2. The non-transitory computer-readable recording medium according to claim 1, wherein
the identifying the adjacent element group includes newly identifying from the heart model and as the adjacent element group, a set of tetra elements adjacent to each tetra element of an element group added to the rendering element group.

3. The non-transitory computer-readable recording medium according to claim 1, wherein
the rendering the heart model includes rendering an internal heart model.

4. A rendering method of rendering calculation results of a heart model on a display device coupled to a computer and executed by a processor provided in the computer, the rendering method comprising generating a histogram of physical values of tetra elements of a rendering element group to be rendered and specified in the heart model including a set of tetra elements each having a physical value for each position to be simulated to detect an allowable range of the physical values, the physical values being values indicative of a behavior of a cardiac muscle of the heart model corresponding to the tetra elements;

identifying from the heart model, an adjacent element group that is a set of tetra elements adjacent to rendering elements included in the rendering element group;

determining whether the physical value of each adjacent element included in the identified adjacent element group is within the allowable range;

adding to the rendering element group, an adjacent tetra element for which the physical value has been determined to be included in the allowable range, the adding including adding to the rendering element group, a tetra element only when the tetra element contacts multiple tetra elements in the rendering element group, the tetra element being of an element group that is among the adjacent element group and determined to be outside the allowable range and the center of gravity of at least any one tetra element among the multiple tetra elements determined to be rendered within a designated distance; and rendering the heart model on the display device according to the rendering element group to which the adjacent element has been added, wherein the rendering the heart model includes rendering the heart model based on the rendering element group post-addition when an element group added to the rendering element group is exhausted.

5. A rendering apparatus that renders simulation results and comprises a computer configured to:

generate a histogram of physical values of tetra elements of a rendering element group to be rendered and specified in the heart model including a set of tetra elements each having a physical value for each position to be simulated to detect an allowable range of the physical values, the physical values being values indicative of a behavior of a cardiac muscle of the heart model corresponding to the tetra elements;

identify from the heart model, an adjacent element group that is a set of tetra elements adjacent to rendering elements included in the rendering element group;

determine whether the physical value of each adjacent element included in the identified adjacent element group is within the allowable range;

add to the rendering element group, an adjacent tetra element for which the physical value has been determined to be included in the allowable range, the adding including adding to the rendering element group, a tetra element only when the tetra element contacts multiple tetra elements in the rendering element group, the tetra element being of an element group that is among the adjacent element group and determined to be outside the allowable range and the center of gravity of at least any one tetra element among the multiple tetra elements determined to be rendered within a designated distance; and render the heart model on the display device according to the rendering element group to which the adjacent element has been added, wherein the rendering the heart model includes rendering the heart model based on the rendering element group post-addition when an element group added to the rendering element group is exhausted.

\* \* \* \* \*